US010345206B2

(12) United States Patent
Stoecker et al.

(10) Patent No.: US 10,345,206 B2
(45) Date of Patent: Jul. 9, 2019

(54) METHOD AND DEVICE FOR TRANSFERRING LIQUIDS

(71) Applicant: EUROIMMUN Medizinische Labordiagnostika AG, Luebeck (DE)

(72) Inventors: Winfried Stoecker, Gross Groenau (DE); Alexander Kowtun, Luebeck (DE); Bianca Huth, Dassow (DE); Lars Koschinat, Warnsdorf (DE); Lars Richter, Luebeck (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 132 days.

(21) Appl. No.: 15/321,765

(22) PCT Filed: Jun. 18, 2015

(86) PCT No.: PCT/EP2015/001230
§ 371 (c)(1),
(2) Date: Dec. 23, 2016

(87) PCT Pub. No.: WO2015/197176
PCT Pub. Date: Dec. 30, 2015

(65) Prior Publication Data
US 2017/0128945 A1 May 11, 2017

(30) Foreign Application Priority Data
Jun. 27, 2014 (EP) ..................... 14002201

(51) Int. Cl.
*B01L 3/00* (2006.01)
*B01L 3/02* (2006.01)
(Continued)

(52) U.S. Cl.
CPC ............... *G01N 1/38* (2013.01); *B01J 4/001* (2013.01); *B01L 3/0296* (2013.01);
(Continued)

(58) Field of Classification Search
CPC ....... A61B 17/06066; A61B 2017/061; A61M 2039/0081; B01L 2300/044; B01L 3/523;
(Continued)

(56) References Cited

U.S. PATENT DOCUMENTS 2,960,122 A * 11/1960 Fuller ....................... B64B 1/62
141/317
2001/0053891 A1 12/2001 Ackley
(Continued)

FOREIGN PATENT DOCUMENTS

CN 102186590 9/2011
EP 1 525 918 A2 4/2005
(Continued)

OTHER PUBLICATIONS

European Search Report dated Dec. 10, 2014 in Patent Application No. 14002201.3 (with English translation of categories of cited documents).
(Continued)

*Primary Examiner* — Christopher Adam Hixson
(74) *Attorney, Agent, or Firm* — Grüneberg and Myers PLLC

(57) ABSTRACT

The present invention relates to a pressure-tight storage vessel containing a liquid, wherein the storage vessel has an inner floor and an upper side and is closed in a pressure-sealing manner by a closure, and wherein the nature of the storage vessel allows pressure-sealing piercing with at least two hollow needles; and to a method for transferring a liquid from a storage vessel to a reaction vessel, the method comprising the following steps: supplying the storage vessel according to the invention, pressure-sealing piercing with a first hollow needle, which is connected to a rinsing-liquid tank, and pressure-sealing piercing with a second hollow needle, which is connected to the reaction vessel, introduc-
(Continued)

Figure 1:
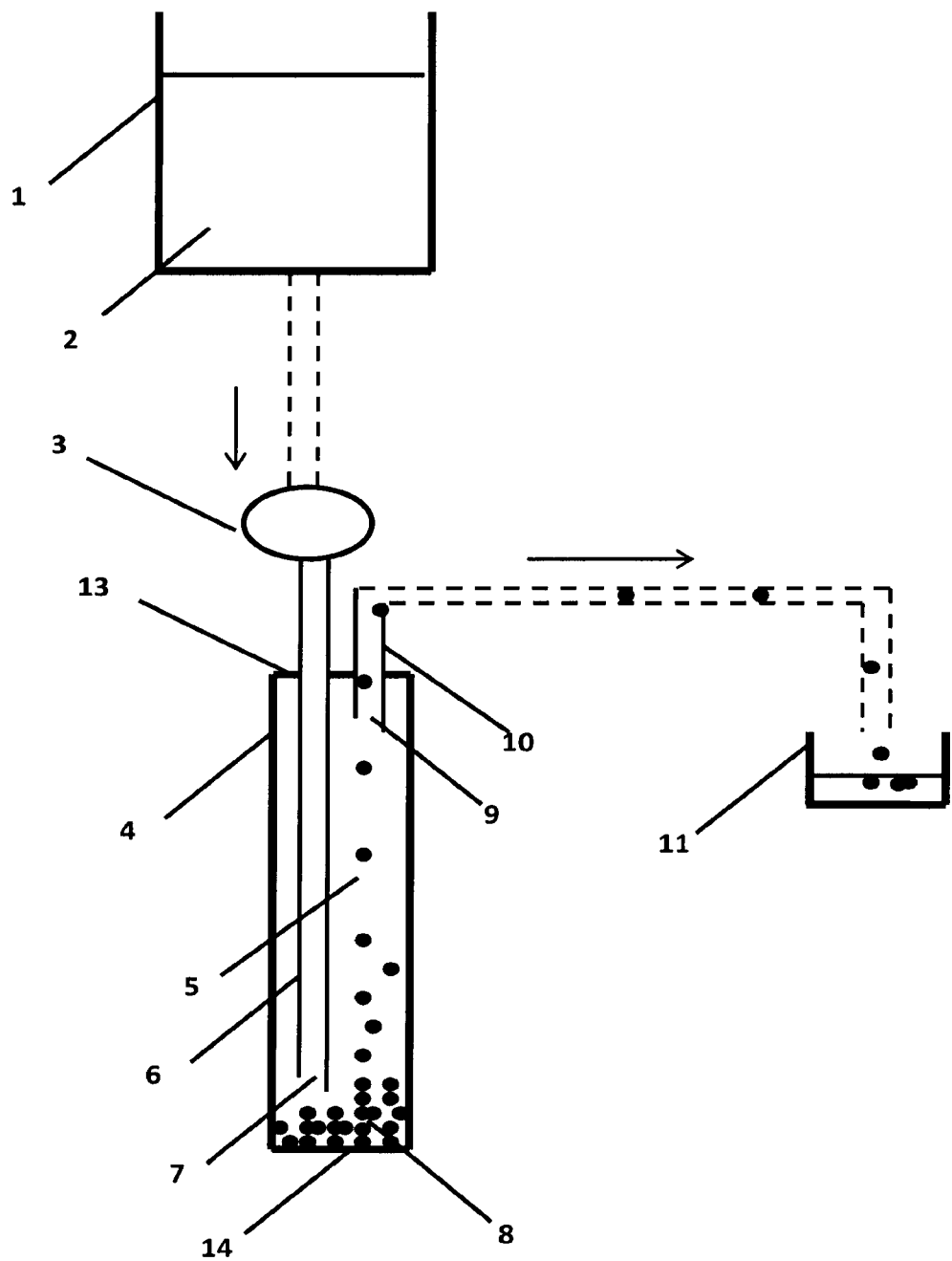

ing rinsing liquid from the rinsing-liquid tank, via the first hollow needle, into the storage vessel, the liquid being driven out of the storage vessel, via the second hollow needle, into the reaction vessel; and to an apparatus which is suitable for implementing the method according to the invention.

16 Claims, 7 Drawing Sheets

(51) Int. Cl.
G01N 1/38 (2006.01)
B01J 4/00 (2006.01)
(52) U.S. Cl.
CPC .............. *B01L 3/50825* (2013.01); *B01L 3/52* (2013.01); *B01L 3/523* (2013.01); *B01L 3/561* (2013.01); *B01L 2200/0647* (2013.01); *B01L 2200/0673* (2013.01); *B01L 2200/0689* (2013.01); *B01L 2200/16* (2013.01); *B01L 2300/044* (2013.01); *B01L 2300/046* (2013.01); *B01L 2300/0832* (2013.01); *B01L 2400/0478* (2013.01)
(58) Field of Classification Search
CPC .... B01L 3/561; B01L 3/0296; B01L 3/50825; B01L 3/52; B01J 4/001; B01J 4/002; G01N 1/38
See application file for complete search history.

(56) References Cited

U.S. PATENT DOCUMENTS

| 2003/0178092 A1* | 9/2003 | Birmingham .......... A63B 41/12 141/38 |
| 2004/0256331 A1 | 12/2004 | Arking et al. |
| 2006/0032746 A1 | 2/2006 | Knott et al. |
| 2006/0121624 A1* | 6/2006 | Huang .................. B01L 3/0289 436/180 |
| 2010/0238287 A1 | 9/2010 | Arking et al. |
| 2015/0153257 A1 | 6/2015 | Olivier et al. |

FOREIGN PATENT DOCUMENTS

| WO | 2010/043271 A1 | 4/2010 |
| WO | 2014/005669 A1 | 1/2014 |

OTHER PUBLICATIONS

International Search Report dated Sep. 21, 2015 in PCT/EP2015/001230 filed Jun. 18, 2015.

* cited by examiner

METHOD AND DEVICE FOR TRANSFERRING LIQUIDS

The present invention relates to a pressure-tight storage vessel containing a liquid, wherein the storage vessel has an inner base and an upper side and is closed in a pressure-sealing manner by a closure, and wherein the nature of the storage vessel allows the pressure-sealing plunging of at least two hollow needles;

to a method for transferring a liquid from a storage vessel to a reaction vessel, comprising the steps of providing the storage vessel according to the invention, pressure-sealing plunging of a first hollow needle which is connected to a flushing-liquid reservoir, pressure-sealing plunging of a second hollow needle which is connected to the reaction vessel, introducing flushing liquid from the flushing-liquid reservoir into the storage vessel via the first hollow needle with outward driving of the liquid from the storage vessel into the reaction vessel via the second hollow needle, and to a device suitable for carrying out said method.

For a multiplicity of technical processes in the fields of chemistry, biotechnology, pharmacy and medicine, it is necessary to use multiple liquid reagents, each of which are only producible or fillable with great effort. It is, then, sensible not to freshly produce each of said reagents for each process run, but to prepare, in one pass, a quantity which is sufficient for multiple runs and which can then be stored in appropriate portions until use.

Apart from economical and logistical advantages, this leads, specifically in the field of medicine, more precisely laboratory diagnostics, to the minimization of error susceptibility of the entire system, since practically identical reagents can be used for each run of the desired diagnostic method. If a result is ambiguous, it can be easily checked whether a deficient quality of the reagents used was the cause of the ambiguity.

However, the trend toward miniaturization in the area of analytics and diagnostics—the reduction in size of reaction preparations down to the absolutely required minimum volume in order to save the frequently high-priced reagents—complicates portioning, especially when the individual portion has a low volume and, in extreme cases, comprises only a few microliters. The smaller the volume, the higher the relative loss upon transfer of the liquid phase from one container to the other as a result of nonspecific adsorption to surfaces and as a result of dead volumes inherent to each instrument.

The transfer of low volumes frequently also causes a lower reproducibility of the method, since random effects such as differing evaporation owing to temperature differences, vibrations or technically related variations in the quantities used have a stronger effect on the result.

A particular problem is represented by inhomogeneous liquids, for example suspensions of beads in aqueous solution, the density of which is higher than that of water, meaning that the beads can sink to the bottom. If such an aqueous solution is mixed to homogeneity and then portioned, the proportion of beads in the aqueous phase decreases during portioning until all beads are sedimented. Accordingly, the number of beads per portion drops, and portions filled at the start of portioning have a higher quantity of beads than the ones filled later.

In addition, such beads in a liquid phase attach easily to surfaces, for example beneath the lid of the storage vessel. This too complicates the removal of portions having the same concentration of beads, especially in automated processes in which the situation of the beads within the transport vessel and the complete transfer thereof is not visually checked.

For many miniaturized systems, beads are used as carriers for reagents. For example, they can, in the field of immunodiagnostics, be carriers for immobilized antigens, to which antibodies to be detected in human samples bind. If such beads are incubated with a liquid sample, this leads to the formation of the antigen/antibody complex, which is immobilized on the bead, if the antibodies are present. After a wash step, said complex can be detected using appropriate reagents, for example a labeled secondary antibody. The commercially available random access analyzers are based on this principle. The beads are usually supplied in aqueous solutions and stored until use.

Thus, there is a need for an automatable system for the quantitative transfer—i.e., transfer which is as complete as possible—of a low-volume liquid from a storage vessel to a reaction vessel.

In the prior art, this problem has been solved using two approaches: on the one hand, a liquid reagent is not introduced into a storage vessel after production, but is instead introduced directly into the reaction vessel intended for the next method step.

The problem with this approach is that the reaction vessel must have a distinctly larger volume than a storage vessel, since the former must provide room for additional reaction partners, solvents and the like. Storing thus requires considerable space, and this causes difficulties especially in the case of reagents to be kept frozen. In the case of volatile reagents, the additional volume additionally leads to the fact that a portion can escape from the liquid phase into the gas phase. If nothing else, this approach reaches its limits when it is necessary to use multiple stored reagents, i.e., when transfers between multiple vessels are unavoidable.

Another approach for the transfer of inhomogeneous liquids envisages that the latter be constantly kept in motion during transfer, for example by stirring or shaking. The phase is therefore constantly homogenized. Apart from the additional expenditure in terms of apparatus and the space requirements for the homogenization process, for example in the form of an additional stirrer, specifically in the parallel processing of a multiplicity of samples, this does not, however, solve the problem of dead volumes. On the contrary, the storage vessel for stirring must be large enough in order to accommodate a stirring magnet, and this causes larger minimum and dead volumes.

Against this background, it is an object of the present invention to provide a device which makes it possible to transfer a liquid from one storage vessel to another vessel with minimal losses, ideally in a quantitative manner. This especially applies to cases where the liquid is inhomogeneous and, for example, contains solids such as particles or beads. In a preferred embodiment, the term "inhomogeneous liquid phase" means that the liquid phase comprises not only a liquid main constituent but also at least one further constituent in a phase separate therefrom, for example a further liquid which does not mix with the liquid main constituent, or a solid.

It is a further object of the present invention to provide a device for carrying out analytical detection methods, wherein the space requirements, the loss of liquid and/or the duration of transfer or of the entire detection method are reduced compared to the methods described in the prior art, whereas reproducibility is increased.

This and further objects are achieved by the subject matter of the present application and especially also by the subject matter of the attached independent claims, with embodiments being revealed by the dependent claims.

In a first aspect, the object of the invention is achieved by a pressure-tight storage vessel containing a liquid, wherein the storage vessel has an inner base and an upper side and is closed in a pressure-sealing manner by a closure, and wherein the nature of the storage vessel allows the pressure-sealing plunging of at least two hollow needles.

In a first preferred embodiment of the first aspect, the storage vessel has an inner height H and the inner base thereof has a diameter D and the ratio of D to H is at least 1:2, preferably 1:5, more preferably 1:10.

In a second preferred embodiment, which is also a preferred embodiment of the first preferred embodiment, the storage vessel comprises a cylindrical interior space.

In a third preferred embodiment, which is also a preferred embodiment of the first to second preferred embodiment, the closure allows the pressure-sealing plunging of a hollow needle, wherein the closure is preferably a lid composed of plastic or aluminum, more preferably in the form of a film.

In a fourth preferred embodiment, which is also a preferred embodiment of the first to third preferred embodiment, the storage vessel comprises a first and a second pressure-sealingly plunged hollow needle.

In a second aspect, the object of the invention is achieved by a method for transferring a liquid from a storage vessel to a reaction vessel, comprising the steps of
  a) providing the storage vessel according to the invention,
  b) pressure-sealing plunging of a first hollow needle which is connected to a flushing-liquid reservoir, and
  c) pressure-sealing plunging of a second hollow needle which is connected to the reaction vessel, and
  d) introducing flushing liquid from the flushing-liquid reservoir into the storage vessel via the first hollow needle with outward driving of the liquid from the storage vessel into the reaction vessel via the second hollow needle.

In a first preferred embodiment of the second aspect, the method according to the invention further comprises
  e) contacting of the liquid in the reaction vessel with at least one reactant with execution of a reaction, and
  f) optionally at the same time or afterwards: detecting the reaction.

In a third aspect, the object of the invention is achieved by a device for transferring a liquid from a storage vessel to a reaction vessel, comprising
  a storage vessel according to the invention, which is connected to a first hollow needle via a feed line,
  a means for holding the storage vessel,
  a reaction vessel which is connected to a second hollow needle via a feed line,
  a flushing-liquid reservoir,
  a means for pumping the liquid,
  a means for plunging the first hollow needle into the storage vessel,
  a means for plunging the second hollow needle into the storage vessel,
  optionally at least one means for detection of the reaction in the reaction vessel,
  wherein the first and the second hollow needle are configured for the pressure-sealing plunging into the storage vessel and for the transfer of liquid, from the flushing-liquid reservoir to the storage vessel in the case of the first hollow needle and from the storage vessel to the reaction vessel in the case of the second hollow needle.

In a fourth aspect, the object of the invention is achieved by the use of the storage vessel according to the invention for storing, transporting and/or transferring a liquid, wherein the liquid is driven, by means of introducing a flushing liquid via a first pressure-sealingly plunged hollow needle, from a pressure-tight storage vessel into a reaction vessel via a second pressure-sealingly plunged hollow needle.

In a preferred embodiment of all aspects and embodiments, the liquid is an inhomogeneous liquid phase, preferably an aqueous solution comprising beads.

In a preferred embodiment of all aspects and embodiments, the liquid is a homogeneous liquid phase, preferably comprising a biological or chemical agent in aqueous solution or a liquid sample, particularly preferably a blood sample, most preferably serum.

In a preferred embodiment of all aspects and embodiments, the first hollow needle, preferably additionally also the second hollow needle, has been or is plunged through the upper side of the storage vessel, preferably through a closure situated therein, more preferably a lid.

In a preferred embodiment of all aspects and embodiments, the first and the second hollow needle have been or are plunged in the form of a coaxial needle.

In a preferred embodiment of all aspects and embodiments, the escape opening of the first hollow needle is located in the bottom quarter of the storage vessel and the escape opening of the second hollow needle is located in the top quarter of the storage vessel.

In a preferred embodiment of all aspects and embodiments, the escape opening of the first hollow needle is configured such that the flow of the introduced flushing liquid branches and a portion thereof is directed in the direction of the upper side and another portion thereof is directed in the direction of the inner base.

The invention is based on the surprising finding from the inventors that a liquid can be transferred in an automatable and reproducible manner using the storage vessels, devices and methods according to the invention, even in the technically demanding case of it comprising an inhomogeneous phase. A deposition of solids, for example beads, is avoided and a deposition in flow-inaccessible corners is prevented.

The invention is further based on the surprising finding from the inventors that a practically quantitative transfer of the liquid is possible according to the invention, making it possible, in the case of diagnostic methods, to minimize the consumption of reagents to be produced elaborately, such as antibody solutions, or of samples available only in limited quantities, for example blood samples from deceased patients.

The invention concerns the transfer of a liquid which is contained in a storage vessel. In a preferred embodiment, the term "liquid", as used herein, is understood to mean a substance or a substance mixture which, at 20° C. and under atmospheric pressure, consists of a liquid to an extent of at least 10, preferably 20, 30, 40, 50, 75, percent by weight, which liquid can, however, be inhomogeneous, especially to the effect that it contains solids. The liquid is in the liquid state for carrying out the method according to the invention, but can also be stored in the storage vessel in the frozen state. The storage vessel is preferably largely filled with liquid, i.e., for example to an extent of at least 75%, 80%, 90% or 95%. The gas phase can consist of air or comprise a chemically inert protective gas, for example argon or nitrogen. The volume of the storage vessel can be from 5 µl to 1 L, preferably from 10 µl to 10 ml, more preferably from 20 μl to 5 ml, more preferably from 25 μl to 1 ml, most preferably from 30 μl to 250 μl.

For the method according to the invention, it is essential that the storage vessel is pressure-tight. Furthermore, the nature of said storage vessel is such that it allows the pressure-sealing plunging of two hollow needles, preferably hollow needles which are stainless steel tube sections sharpened by grinding. Preferably, the outer diameter thereof is from 0.5 to 5 mm, particularly preferably 1 mm, and its inner diameter is from 0.1 to 3 mm, particularly preferably from 0.2 to 0.7 mm, with the proviso that the inner diameter is smaller than the outer diameter. For example, the vessel can have a wall composed of a 0.3 mm thick layer of a suitable plastic, such as polyethylene. Such vessels can be obtained by injection molding. The vessel has a closure which consists of the same material as the wall or of a different material and can be opened in a reversible or irreversible manner. For example, the closure can be a screw cap or a hinged lid. Similarly, the closure of a plastics container is possible with a film composed of a different material, for example a plastics film or an aluminum film. The thickness of the film can be from 5 μm to 5 mm, preferably from 10 μm to 1 mm, more preferably from 25 μm to 250 μm. Furthermore, one possibility for a closure is a window closable with a septum, for example a silicone seal.

In a particularly preferred embodiment, the two hollow needles have been or are plunged centrally relative to the longitudintal axis of the storage vessel. This means that the point on the longitudinal axis that is between the plunge point of the first hollow needle and the plunge point of the second hollow needle and has the same distance from the two plunge points on the longitudinal axis, also has the same distance from the two ends of the storage vessel along the longitudinal axis thereof, wherein, in the case of the latter distance, a deviation is possible, i.e., an extension of the distance of the plunge site of the first hollow needle from the end of the storage vessel that is facing it and a corresponding shortening of the distance of the plunge site of the second hollow needle from the other end of the storage vessel of up to 30%, preferably 20%, 15%, 10%, most preferably 5%, of the length of the longitudinal axis.

The liquid can be a solution of biological or chemical agents, or a sample of human or animal origin that contains a reactant to be detected. Particularly preferably, the liquid is a sample comprising a body fluid selected from the group comprising serum, urine, cerebrospinal fluid or saliva or a dilution or processed form thereof. Alternatively, the liquid can be a sample composed of foodstuffs, beverages, drinking or bath water, stool, soil material or the like. Preferably, the sample is appropriately processed, for example by centrifugation of nonsoluble blood constituents in the case of a blood sample, and/or made stable after it has been obtained.

The storage vessel has an inner base and an inner height H, this being understood to mean the base geometrically accessible to the liquid present and, respectively, the height of the side wall accessible to the liquid. Preferably, the vessel has a highest possible ratio of inner height to inner base, measured in the form of the inner diameter D thereof, and so there is a smallest possible inner base area for the adsorption of sedimented substances on the base. The ratio of D to H is preferably at least 1:2, 1:2.5, 1:3, 1:4, 1:5, 1:7.5, 1:10, 1:15 or 1:20, wherein the longitudinal axis runs along the longer side and has two ends. The upper side is situated at one of the ends. The upper side is preferably at the end which is at the top in the orientation predetermined by the shape of the storage vessel when using the storage vessel. The inner base preferably has a circular shape, and so deposits in flow-inaccessible corners are avoided, as does the vertically opposing inner lid. By contrast, preference is given to designing at least the outer shape of base and/or upper side of the storage vessel with corners, for example in the form of a square, in order to facilitate gripping and holding the vessel in a certain orientation.

According to the invention, a first and a second hollow needle are plunged into the storage vessel. The first hollow needle serves for feeding preferably a flushing liquid, the second for discharging the liquid. Both hollow needles are plunged in a pressure-sealing manner and preferably have the same diameter, and so the introduction of a flushing liquid brings about the escape of an equivalent volume of liquid via the second hollow needle. In a preferred embodiment, the storage vessel is said to be pressure-tight when the introduction of 1 ml of water into the completely filled storage vessel for 100 seconds via a pressure-sealingly plunged hollow needle brings about the escape of at least 900 μl, preferably 950 μl, more preferably 990 μl, of water in the same time via a second pressure-sealingly plunged hollow needle of the same construction. Preferably, plunging is said to be executed in a pressure-sealing manner when the storage vessel remains pressure-tight upon closure of the plunged hollow needle. The diameter of the hollow needles must be of such a value that any solids present in the liquid, such as beads, cannot clog the needles.

As hollow needle, it is possible to use any device which consists of a material suitable for plunging and has a hollow channel via which liquid is driven in or driven out. Preferably, the hollow needle is one composed of metal. Alternatively, it is possible to use a sufficiently hard, sharpened glass or plastics cannula.

The position of the escape openings of the first and the second hollow needle in the storage vessel is selected such that circulation of the liquid is maximized. What must be avoided is a short circuit in which liquid escaping from the first hollow needle directly enters the second hollow needle without appreciable migration through the volume of the liquid. Accordingly, it is appropriate to position the escape opening of the first hollow needle and the entrance opening of the second hollow needle such that the distance of the two openings from one another is maximized. This can be set via the selection of the plunge site for both hollow needles, the length by which the two hollow needles protrude into the storage vessel, or the shape of the storage vessel, for example the insertion of a partition wall which maximizes the route which must be covered by the liquid flow between the hollow needles. In a particularly preferred embodiment, both the first and the second hollow needle are plunged through the closure of the storage vessel via the upper side, but the first hollow needle protrudes distinctly further into the storage vessel, to just above the base, whereas the second hollow needle barely protrudes into the storage vessel via the plunge site. In this way, the liquid flow entering the storage vessel directly hits beads situated on the base, swirls them up, and minimizes deposition at the base.

Particular preference is given to realizing the two hollow needles in the form of a double needle in which both needles are joined with the same orientation with parallel arrangement at least along the longitudinal axis, for example by soldering together of two metal hollow needles, or in the form of a coaxial needle. In the latter case, the first hollow needle has a smaller diameter than the second hollow needle and is arranged concentrically in the inner space thereof, with the first hollow needle being longer than the second and protruding far from the escape opening thereof such that there is no short circuit. If first and second hollow needle are joined to one another with parallel arrangement and the same orientation, they can be advantageously plunged together into the storage vessel.

In a further preferred embodiment, one hollow needle, preferably the first, is plunged into the storage vessel via the upper side, and the other hollow needle, preferably the second, is plunged through the base from below. In this way, the flow of the flushing liquid can act synergistically with gravity. This arrangement is recommendable especially when transferring a liquid having a homogeneous phase, in which no solids are collected in corners through which flow is poor.

Optionally, there is the option of plunging at least one further hollow needle in a pressure-sealing manner in addition to the first and the second hollow needle. For example, the flushing liquid can be additionally introduced into the storage vessel via a third hollow needle in order to better distribute the flow within the storage vessel and to prevent the deposition of solids in the liquid. In this case, the escape openings of the first and the third hollow needle can be positioned and oriented such that the flushing liquid escaping therefrom flows in the direction of the base or of the upper side of the storage vessel, preferably such that it emerges vertically, whereas the escape opening of the second hollow needle is, relative to the longitudinal axis of the storage vessel, positioned symmetrically between the other two escape openings.

The escape opening of a hollow needle, preferably of the first hollow needle, can optionally be designed such that the stream of the liquid escaping therefrom is divided so that it is directed in at least two different directions, optionally even in more than two directions. This can be established by multiple, appropriately oriented escape openings at the end of the hollow needle. This is useful especially in the case of a first hollow needle when flushing liquid is introduced into the storage vessel there via and the escape opening is positioned close to the inner base or to the upper side in order to allow a uniform flow through the vessel and to prevent a deposition of solids present in the liquid. In the case of a divided stream of the liquid, the first hollow needle is preferably plunged centrally along the longitudinal axis; more preferably, the second hollow needle is also plunged centrally. Short circuit is then prevented by the ends of the two hollow needles being at different points along the transverse axis of the storage vessel, which points are as far apart as possible from one another along the transverse axis. For example, the end of the first hollow needle, from which liquid escapes, can be just in front of the wall opposing the plunge site, whereas the end of the second hollow needle is, along the transverse axis, close to the plunge site.

According to the invention, a liquid is conducted from the flushing-liquid reservoir into the storage vessel via the first hollow needle. Feeding between flushing-liquid reservoir and first hollow needle and between second hollow needle and reaction vessel proceeds via means suitable for this purpose, for example chemically inert, pressure-tight plastics hoses. Therebetween, it is possible to connect further vessels or devices for processing the liquid, for example for adjusting temperature.

In a preferred embodiment, the liquid is conducted under pressure into the storage vessel via the first hollow needle. In the simplest case, the pressure can be generated by gravity with storage of the liquid reservoir above the storage vessel. However, preference is given to a generation of pressure via an appropriate device, for example a pump. The pressure which builds up in the storage vessel drives the liquid present therein out of the storage vessel via the entrance opening of the second hollow needle. Alternatively, it is also possible to apply negative pressure on the side of the second hollow needle.

After plunging of the needles, liquid is introduced into the storage vessel and the original content thereof is driven out. To this end, the storage vessel is flushed with liquid until the liquid is transferred. If this is done with sufficient liquid, for example with at least 2, 3, 5, 10, 20, 50 or 100 times the volume of the storage vessel, the transfer can be practically complete. Appropriately, it is concentrated in the storage vessel such that it, after dilution while carrying out the method according to the invention, is present in a concentration suitable for the following reaction.

After transfer, the hollow needles can be removed from the storage vessel and said storage vessel can be removed from the device according to the invention. Preferably, in order to avoid contamination, the storage vessel is a disposable article which can be subsequently disposed of.

The flushing liquid is introduced into the storage vessel at a rate which allows a fastest possible transfer of the liquid phase. On the other hand, said rate must be of such a value that agents present in the solution remain intact and do not, for instance under pressure exposure or as a result of shear forces, precipitate, clump or become impaired in terms of their quality in some other way. For example, the rate can be from 10 to 10 000 µl/s, preferably from 50 to 2000 µl/s, most preferably from 100 to 1000 µl/s.

The flushing liquid can be introduced at a steady rate. However, in a preferred embodiment, especially when transferring an inhomogeneous liquid, there is initially a short phase for whirling up and homogenizing solid components of the liquid phase, followed by the actual transfer. Therebetween, it is possible to set a break, for example from 1 to 60 seconds, from 2 to 30 seconds or from 5 to 15 seconds.

As flushing liquid, it is possible to use any liquid provided that it does not impair the usability of the liquid to be transferred upon contact in the storage vessel and does not impair the reaction in the reaction vessel. In a preferred embodiment, the properties of the flushing liquid, for example density and hydrophobicity, must be selected such that mixing with the liquid to be transferred and the associated dilution is minimized, especially when the latter comprises a homogeneous liquid phase. If the liquid to be transferred is an aqueous solution, a hydrophobic liquid immiscible with water can be used as flushing liquid, and vice versa.

In the device according to the invention, a means for fixing the storage vessel is provided. In the simplest case, said means is an indentation which has been matched to the shape of the storage vessel, and so a storage vessel introduced therein is held in a sufficiently stable manner. Preferably, the storage vessel is additionally fixed with a holder, a clamp or the like to additional points.

Preferably, the device further comprises a transport means, for example a gripper which brings about the removal of the storage vessel from a storage unit and the transport to and the insertion into the fixing means, as well as the removal after the method has been carried out. Generally, the device according to the invention is preferably realized such that all steps of the method according to the invention can be carried out in a fully automated manner from the provision of the storage vessel.

The device according to the invention can be equipped such that a multiplicity, for example at least 2, 4, 8, 10, 20, 50 or 100, of storage vessels can be processed in parallel and their content can be transferred to corresponding reaction vessels. To this end, a corresponding number of sets is present, each comprising a first and a second hollow needle, a holder with storage vessel, and corresponding access means to at least one flushing liquid and at least one reaction vessel. In a preferred embodiment, the term "reaction vessel", as used herein, is to be understood to mean a vessel in which the content of the storage vessel is appropriately processed, typically by means of a chemical or physical interaction.

A particular advantage of the invention is that any desired number and combination of agents can be transferred from various, practically spontaneously selected storage vessels to a reaction vessel.

The device according to the invention is preferably oriented to storing a multiplicity of storage vessels, reagents and, optionally, samples and to combining and to processing them in succession or as required. Suitable storage conditions, for example temperature, humidity, ventilation or, as required, vacuum or chemically inert protective gas, can be set. This allows the operator to have ready a very wide variety of different reagents in a small space for a relatively long time and to use and to combine them spontaneously.

If the liquid to be transferred comprises solids, especially beads, which are diluted in the course of the transfer, but should be present in concentrated form for a subsequent use, then, according to the invention, a concentration is possible after outward driving from the storage vessel but before introduction into the reaction vessel. Concentration can, for example, be brought about by application of negative pressure and removal of liquid or decanting, but particularly preferably by the liquid being conducted through a screen which catches the solids.

Preferably, the device according to the invention comprises a means for detection of a reaction proceeding in the reaction vessel. The nature of the detector depends on the nature of the reaction to be detected. For example, a detection of chemiluminescence, UV-Vis absorption, radioactivity, fluorescence, light scattering, NMR/ESR-active chemical groups, magnetic particles, temperature changes, pH changes, conductivity changes or the like is possible. In a particularly preferred embodiment, the detector is a chemiluminescence-capable detector.

The inventive transfer of liquid can be carried out within the scope of an immunodiagnostic method. In said method, a human or animal sample, preferably blood sample, is tested for the presence of antibodies. Whether an antibody is detectable is a diagnostically important piece of information. Preferably, the antibody is detected as a result of its binding to an antigen which has been immobilized, particularly preferably to beads. Immunodiagnostic assays which work according to this principle have been described in the prior art for numerous indications, for example in EP 2 199 303, DE 10 2009033281, WO 2010/009457 or EP12183919.5.

For the practical procedure, an inventive storage vessel containing beads to which the antigen has been immobilized is provided. To carry out the assay, the liquid containing the beads is transferred according to the invention to a reaction vessel. There, the beads are contacted with the sample and subsequently washed. If antibody was present in the sample, said antibody is immobilized on the beads via its binding to the antigen. This is followed by an incubation with a reagent for detecting the antibody. Said reagent can be a secondary antibody labeled with an enzyme which catalyzes a chemiluminescence reaction, in which light is released. If the complex of antigen, antibody and secondary labeled antibody is present, it can, in a final step after addition of the substrates for the chemiluminescence reaction, be detected in the form of light. Suitable agents have been described in the prior art, for example in Ireland, D., and Samuel, D. (1989), Enhanced chemiluminscence ELISA for the detection for antibody to hepatitis B virus surface antigen, J. Biolum. Chemilumin., 159-163 and in "Acridinium Esters as Highly Specific Activity Labels in Immunoassays," Clin. Chemistry 19: 1474-1478 (1984) and in U.S. Pat. No. 4,842,997 A. Both the antigen-coated beads and the sample, the secondary labeled antibody and the substrates required for the reaction can be transferred according to the invention from storage vessels to a reaction vessel.

The liquid can comprise a homogeneous liquid phase. Preferably, the liquid can be human or animal samples taken for diagnostic testing and optionally processed, for example blood, preferably blood serum, urine, cerebrospinal fluid, saliva or sweat.

However, the liquid can also comprise an inhomogeneous phase and comprise either two liquids which are immiscible or only miscible to a limited extent or a solid substance in a liquid. In a preferred embodiment, the liquid is beads in aqueous solution. Such beads can be provided with biological reagents immobilized thereon, for example in the form of antigen-acting polypeptides. Various beads for numerous applications are commercially available, mainly based on carbohydrate (e.g., agarose) or plastic. They contain active or activatable chemical groups such as carboxyl group, which can be utilized for the immobilization of reagents, for example of antibodies or antigens. Preferably, the beads are beads having an average diameter of from 0.2 µm to 5 mm, from 0.5 µm to 1 mm, from 0.75 µm to 100 µm or from 1 µm to 10 µm. The beads can be coated with an antigen which binds to a diagnostically relevant antibody, or with affinity ligands, for example biotin or glutathione. Preferably, the liquid comprises the beads in the form of an aqueous suspension having a bead content of from 10 to 90%, preferably from 20 to 80%, preferably from 30 to 70%, more preferably from 40 to 60% (w/w).

In a particularly preferred embodiment, the beads are paramagnetic beads, which can be easily concentrated on a surface with the aid of a magnet. For this purpose, commercial paramagnetic beads usually contain a paramagnetic mineral, for example iron oxide. A multiplicity of suitable paramagnetic beads is commercially available.

Regardless of the homogeneity state, an aqueous liquid phase is preferably involved. This can contain suitable additives such as ethanol or azide for preservation, or stabilizers such as pH buffer, glycerol or salts in physiological concentrations, for example for stabilizing biological or chemical agents. A suitable buffer is, for example, 10 mM sodium phosphate, 150 mM sodium chloride, 50% glycerol, and 0.02 (w/v) sodium azide, pH 7.4.

The invention will be elucidated below on the basis of exemplary embodiments with reference to the figures. In every respect, the described embodiments are to be understood merely as examples and not as limiting, and various combinations of the stated features are encompassed by the scope of the invention.

FIG. 1 shows a diagram of the device according to the invention having an upper side (13) and an inner base (14) and having a flushing-liquid reservoir (1) containing flushing liquid (2). Said reservoir is connected via a feed line and via a pumping means (3) to the first hollow needle (6), which protrudes with its escape opening (7) into the storage vessel (4), which contains the liquid to be transferred (5) containing beads (8). The second plunged hollow needle (10) with its escape opening (9) is connected to the reaction vessel (11). The arrows show the direction of the liquid flow.

Figure 2:
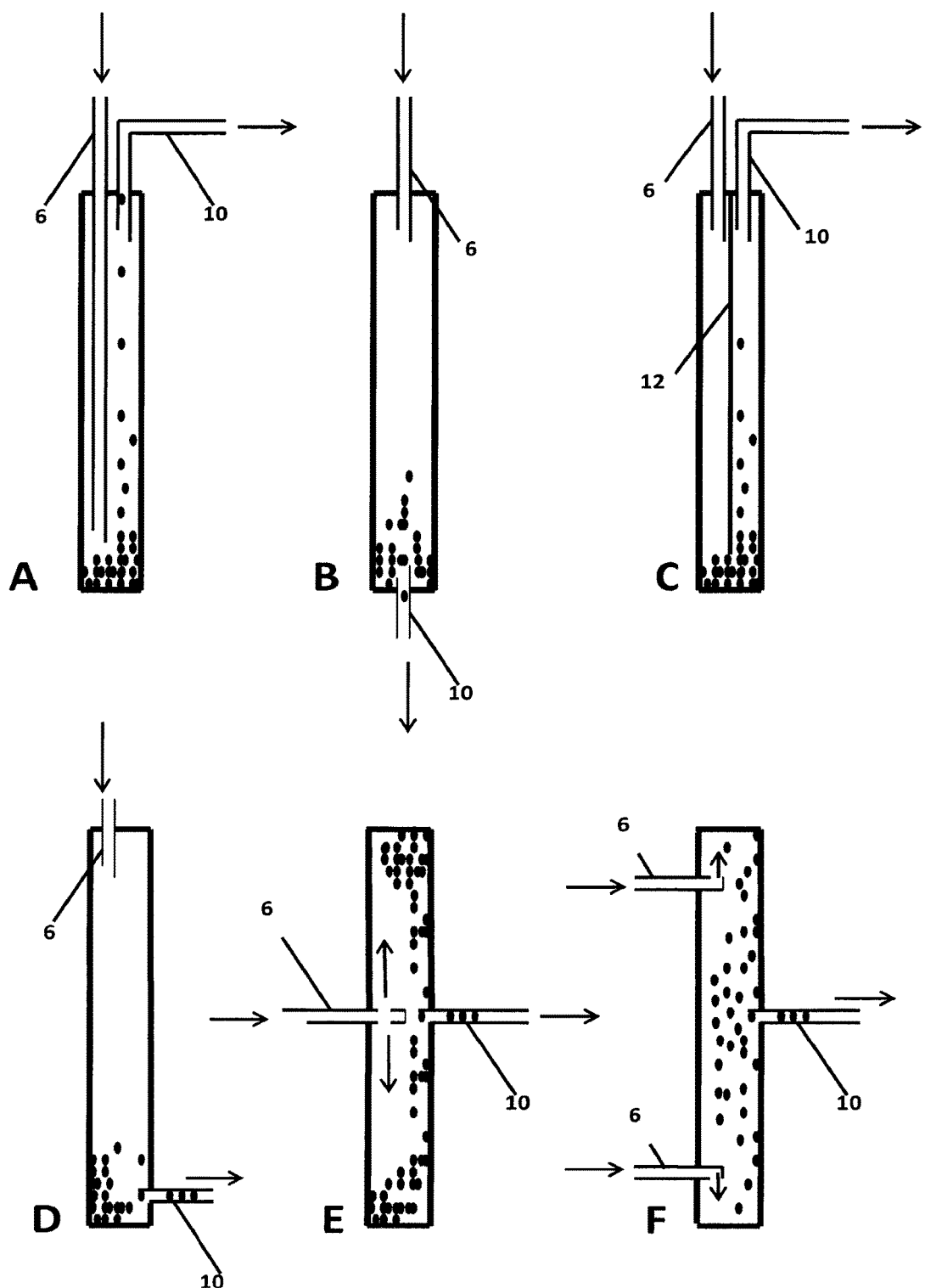
Figure 2:
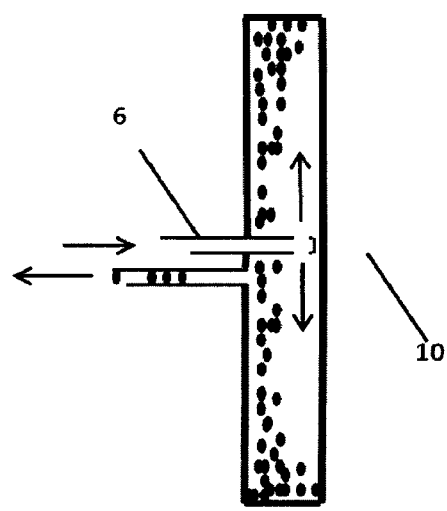

FIG. 2 shows the storage vessel according to the invention with different variants for arranging the plunged hollow needles. The arrows show the direction of the liquid flow.

In FIG. 2A, the first and the second hollow needle have been plunged through the upper side, but the first hollow needle protrudes deep into the storage vessel such that its escape opening is situated close to the inner base.

In FIG. 2B, the first hollow needle has been plunged through the upper side and the second hollow needle has been plunged through the inner base, so the liquid flow runs from top to bottom.

In FIG. 2C, a partition wall (12) has been inserted into the storage vessel, which partition wall prevents a short circuit of the flow between the escape openings of the first and of the second hollow needle, which are both located close to the upper side.

In FIG. 2D, the first hollow needle has been plunged through the upper side and the second has been plunged through the side wall close to the inner base. Since both needles only barely protrude into the vessel, the escape openings are located close to the upper side or close to the inner base.

In FIG. 2E, both hollow needles have been plunged centrally relative to the longitudinal axis of the vessel. Owing to the branching of the flow at the escape opening of the first hollow needle, a short circuit is prevented, however, and one portion of the flow is directed in the direction of the upper side and another portion is directed in the direction of the inner base.

In FIG. 2F, a third plunged hollow needle is additionally used to introduce the flushing liquid in addition to the first hollow needle; the flow of the flushing liquid escaping therefrom is directed in the direction of the upper side or of the inner base in order to prevent the deposition of beads. The second hollow needle has been plunged centrally relative to the longitudinal axis of the storage vessel.

In FIG. 2G, both hollow needles have, from the same direction, been plunged centrally relative to the longitudinal axis of the vessel. A short circuit is prevented owing to the branching of the flow at the escape opening of the first hollow needle and owing to the fact that one of the hollow needles has been plunged only barely beyond the wall and the second has been inserted further until just before the wall opposing the plunge site.

Figure 3:
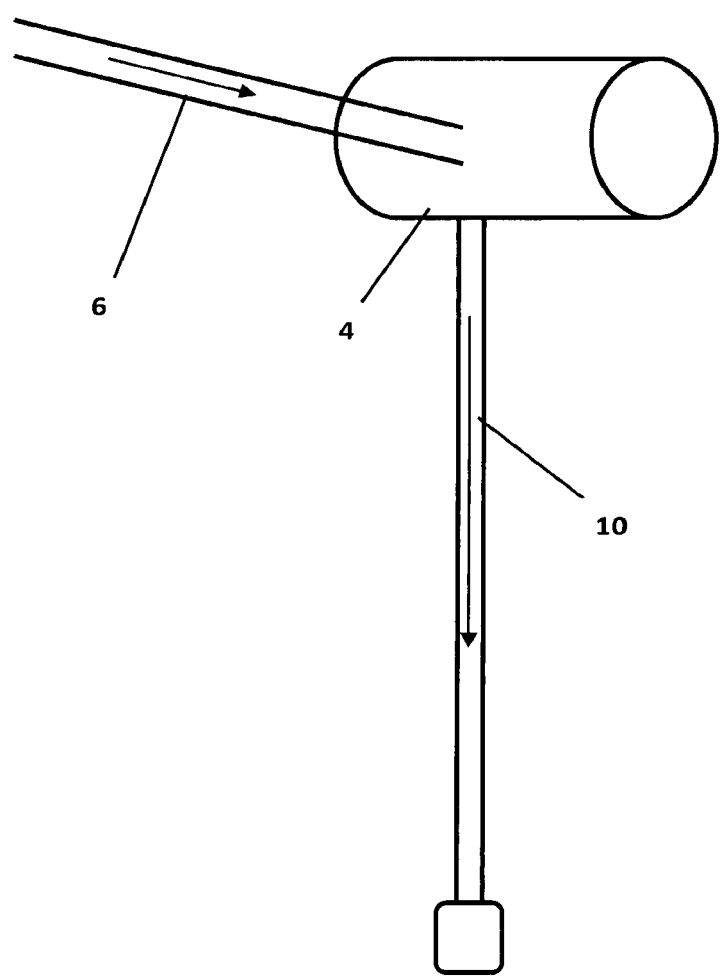

FIG. 3 shows a photo of the storage vessel according to the invention. The first and the second hollow needle have been plunged centrally relative to the longitudinal axis and perpendicularly to one another, projected onto the base plane. The arrows show the direction of the liquid flow.

Figure 4:
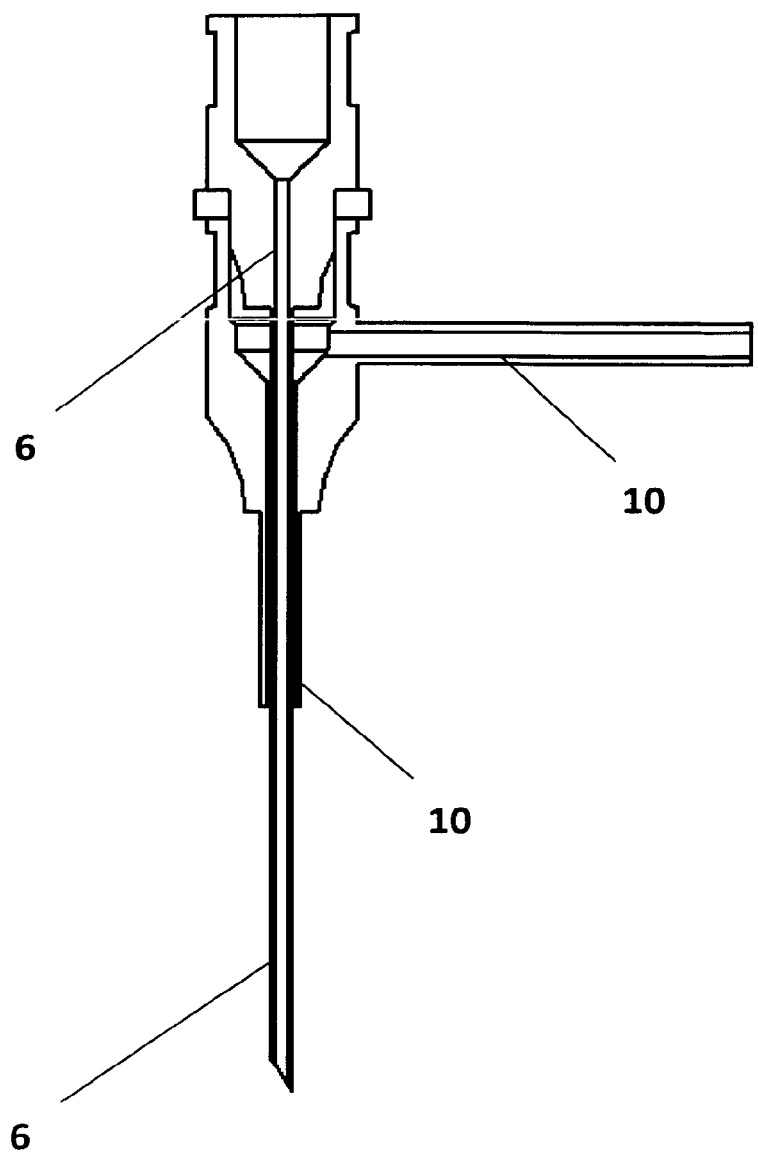

FIG. 4 shows an exemplary coaxial needle usable according to the invention. It can be plunged into the upper side of the storage vessel. The first hollow needle, through which flushing liquid is introduced, is arranged in the interior of the second hollow needle; at the same time, the first hollow needle protrudes distinctly further into the storage vessel in order to prevent a short circuit of the introduced flushing liquid and of the liquid driven out via the entrance opening of the second hollow needle.

Figure 5:
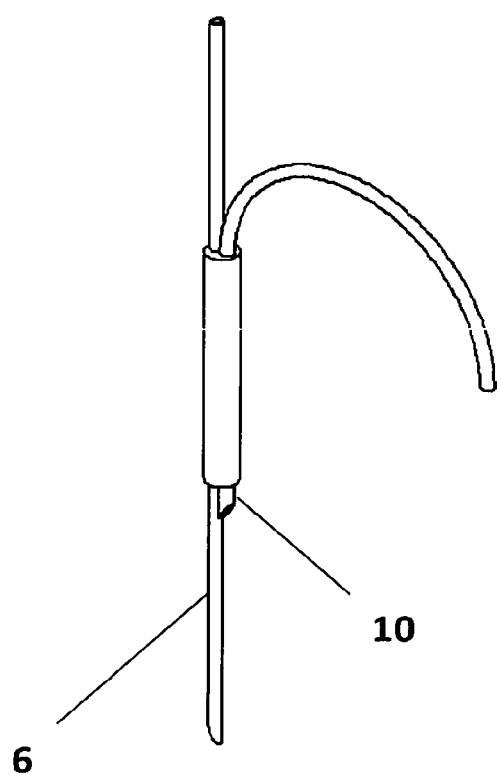

FIG. 5 shows an exemplary double needle usable according to the invention, which can likewise be plunged into the upper side of the storage vessel, for example through a film sealing the upper side. Again, the first hollow needle protrudes distinctly further into the storage vessel in order to prevent a short circuit of the introduced flushing liquid and of the liquid driven out via the entrance opening of the second hollow needle.

Figure 6:
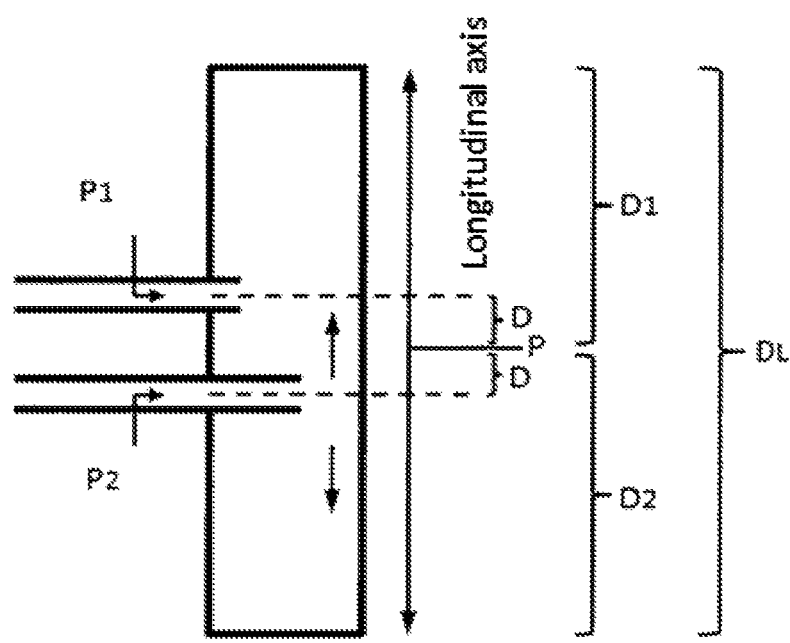

FIG. 6 illustrates the central plunging of the two hollow needles. Point P on the longitudinal axis that is between the plunge point of the first hollow needle P1 and the plunge point of the second hollow needle P2 and has the same distance D from the two plunge points on the longitudinal axis, also has the same distance from the two ends of the storage vessel along the longitudinal axis thereof, wherein, in the case of the latter distance, a deviation is possible, i.e., an extension of the distance of the plunge site of the first hollow needle from the end of the storage vessel that is facing it D1 and a corresponding shortening of the distance of the plunge site of the second hollow needle from the other end of the storage vessel D2.

LIST OF REFERENCE SIGNS

1 Flushing-liquid reservoir
2 Flushing liquid
3 Means for pumping
4 Storage vessel
5 Liquid
6 First hollow needle
7 Escape opening of the first hollow needle
8 Beads
9 Escape opening of the second hollow needle
10 Second hollow needle
11 Reaction vessel
12 Partition wall
13 Upper side
14 Inner base

The invention claimed is:

1. A method for transferring a liquid from a storage vessel to another vessel, comprising
   a) providing the storage vessel containing the liquid,
   wherein the storage vessel has an inner base and an upper side and is closed in a pressure-sealing manner by a closure,
   wherein the nature of the storage vessel allows the pressure-sealing plunging of at least two hollow needles, and
   wherein each of the hollow needles has an escape opening,
   b) pressure-sealing plunging of a first hollow needle which is connected to a flushing-liquid reservoir, and
   c) pressure-sealing plunging of a second hollow needle which is connected to the other vessel,
   d) introducing flushing liquid from the flushing-liquid reservoir into the storage vessel via the first hollow needle with outward driving of the liquid from the storage vessel into the other vessel via the second hollow needle,
   wherein the escape opening of the first hollow needle is configured such that the flow of the introduced flushing liquid branches and a portion thereof is directed in the direction of the upper side and another portion thereof is directed in the direction of the inner base or wherein, in addition to the first hollow needle, a third hollow needle is used to introduce the flushing liquid,
   wherein the flow of the flushing liquid escaping therefrom is directed in the direction of the upper side or in the direction of the inner base.

2. A method for storing, transporting and/or transferring a liquid, comprising:
   filling the liquid in a storage vessel,
   wherein the storage vessel has an inner base and an upper side and is closed in a pressure-sealing manner by a closure, wherein the nature of the storage vessel allows the pressure-sealing plunging of at least two hollow needles, for storing, transporting and/or transferring a liquid, wherein each of the hollow needles has an escape opening, wherein the liquid is driven, by introducing a flushing liquid via a first and a second pressure-sealingly plunged hollow needle, from a pressure-tight storage vessel into another reaction vessel, wherein the escape opening of the first hollow needle is configured such that the flow of the introduced flushing liquid branches and a portion thereof is directed in the direction of the upper side and another portion thereof is directed in the direction of the inner base or wherein, in addition to the first hollow, needle, a third hollow, needle is used to introduce the flushing liquid, wherein the flow of the flushing liquid escaping therefrom is directed in the direction of the upper side or in the direction of the inner base.

3. The method as claimed in claim 1, further comprising:
e) contacting of the liquid in the other vessel with at least one reactant with execution of a reaction, and
f) optionally, at the same time or afterwards: detecting the reaction.

4. The method of claim 1, wherein the storage vessel has an inner height H and the inner base thereof has a diameter D, and
a ratio of D to H is at least 1:2.

5. The method of claim 1, wherein the storage vessel comprises a cylindrical interior space.

6. The method of claim 1,
wherein the liquid in the storage vessel is an inhomogeneous liquid phase.

7. The method of claim 1,
wherein the liquid in the storage vessel is a homogeneous liquid phase.

8. The method of claim 1,
wherein at least the first hollow needle has been or is plunged through the upper side of the storage vessel.

9. The method of claim 1,
wherein the first and the second hollow needles are plunged in the form of a coaxial needle.

10. The method of claim 1,
wherein the escape opening of the first hollow needle is located in the bottom quarter of the storage vessel and the escape opening of the second hollow needle is located in the top quarter of the storage vessel.

11. The method of claim 1,
wherein the storage vessel has an inner height H and the inner base thereof has a diameter D, and
a ratio of D to H is at least 1:5.

12. The method of claim 1,
wherein the storage vessel has an inner height H and the inner base thereof has a diameter D, and
a ratio of D to H is at least 1:10.

13. The method of claim 6, wherein the liquid in the storage vessel is an aqueous solution comprising beads.

14. The method of claim 7, wherein the liquid in the storage vessel comprises a biological or chemical agent in aqueous solution or a liquid sample.

15. The method of claim 1, wherein the method does not comprise stirring or shaking.

16. The method of claim 2, wherein the method does not comprise stirring or shaking.

* * * * *